United States Patent [19]

Asato et al.

[11] 4,060,627

[45] Nov. 29, 1977

[54] SUBSTITUTED TETRAHYDROIMINOBENZO(b)THIEN-4-YLUREAS AS NOVEL GROWTH PROMOTING COMPOUNDS FOR ANIMALS

[75] Inventors: Goro Asato, Titusville; Terence James Bentley, Cranbury, both of N.J.

[73] Assignee: American Cyanamid Company, Stamford, Conn.

[21] Appl. No.: 622,298

[22] Filed: Oct. 14, 1975

[51] Int. Cl.$^2$ .................. A61K 31/38; C07D 333/16
[52] U.S. Cl. .................. 424/275; 260/329 AM; 260/332.3 P
[58] Field of Search ............... 424/275; 260/332.2 R, 260/332.5, 329 F, 332.3 P, 329 AM

[56] References Cited

U.S. PATENT DOCUMENTS

| | | | |
|---|---|---|---|
| 3,776,924 | 12/1973 | Lundberg et al. | 260/332.2 R |
| 3,793,452 | 2/1974 | Strong et al. | 424/275 |
| 3,855,242 | 12/1974 | Chapman et al. | 424/275 |

*Primary Examiner*—V. D. Turner
*Attorney, Agent, or Firm*—Edward A. Conroy, Jr.

[57] ABSTRACT

This disclosure describes novel 4,5,6,7-tetrahydro-7-iminobenzo[b]thien-4-ylureas, methods of preparation thereof, and methods of use of said compounds for enhancing feed efficiency and for promoting the growth rate of veterinary homothermic animals.

23 Claims, No Drawings

SUBSTITUTED TETRAHYDROIMINOBENZO(B)THIEN-4-YLUREAS AS NOVEL GROWTH PROMOTING COMPOUNDS FOR ANIMALS

BRIEF SUMMARY OF THE INVENTION

This invention relates to novel substituted 4,5,6,7-tetrahydro-7-iminobenzo[b]thien-4-ylureas and, more particularly, is concerned with compounds which may be represented by the following general formula:

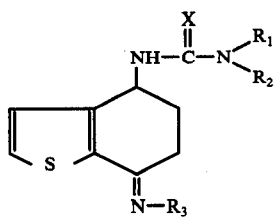
(IA)

wherein X is oxygen or sulfur; $R_1$ is hydrogen or alkyl having up to 4 carbon atoms; $R_2$ is hydrogen, hydroxy, alkyl having up to 4 carbon atoms, alkoxy having up to 4 carbon atoms, allyl, 2-propynyl or benzyl; $R_3$ is a moiety selected from the group consisting of those of the formulae:

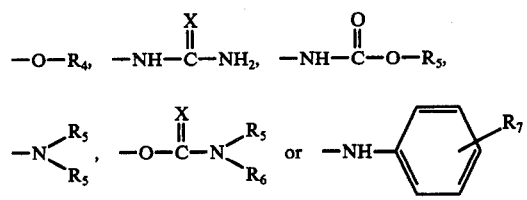

wherein X is oxygen or sulfur; $R_4$ is hydrogen, alkyl having up to 4 carbon atoms or benzyl; $R_5$ is alkyl having up to 4 carbon atoms; $R_6$ is hydrogen or alkyl having up to 4 carbon atoms; and $R_7$ is hydrogen, chloro, methyl or methoxy. Since the compounds of formula (IA) have an asymmetric carbon atom at the 4-position, the present invention includes the optical isomers as well as the racemic mixtures of the compounds of formula (IA).

A preferred embodiment of the present invention consists of the optically active (S) isomers represented by the following general formula:

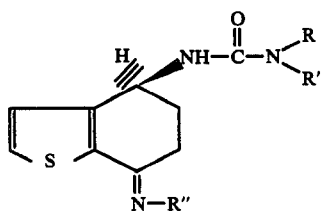
(IB)

wherein R is hydrogen or methyl; R' is hydrogen or alkyl having up to 4 carbon atoms; R" is a moiety selected from the group consisting of those of the formulae:

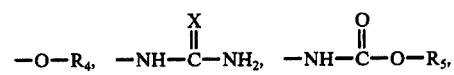

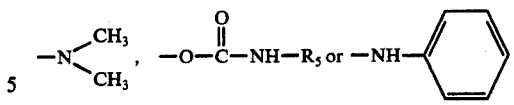

wherein X, $R_4$ and $R_5$ are as hereinabove defined. This invention also relates to methods for the preparation of the hereinabove identified formula (IA) tetrahydro-7-iminobenzo[b]thien-4-ylurea compounds, which may be the racemic mixtures or the optical isomers thereof.

In accordance with this invention, formula (IA) 4,5,6,7-tetrahydro-7-iminobenzo[b]thien-4-ylurea compounds wherein $R_1$ to $R_7$ and X are as hereinabove defined (wherein said compounds may be the racemic mixtures or the optical isomers thereof) may be conveniently prepared from the corresponding 4,5,6,7-tetrahydro-7-oxobenzo[b]thien-4-ylurea compounds represented by the formula (II) below:

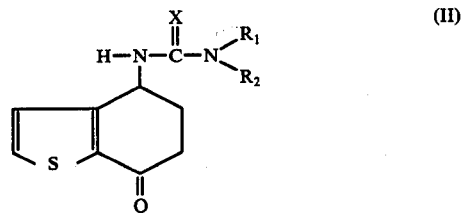
(II)

wherein $X_1$, $R_1$ and $R_2$ are as hereinabove defined, by a number of routes hereinbelow described and illustrated in detail.

Advantageously, a formula (IA) tetrahydro-7-iminobenzo[b]thien-4-ylurea compound (wherein $R_3$ is $-OR_4$ and $R_1$ and $R_2$ are as defined above) can be prepared by reacting 1 mole equivalent of a formula (II) tetrahydro-7-oxobenzo[b]thien-4-ylurea with a 1 to 1.2 mole equivalent of a compound of the formula:

$$H_2N\text{-}OR_4$$

or an acid addition salt (preferably the hydrochloride) thereof (wherein $R_4$ is as defined above) in anhydrous pyridine under a nitrogen atmosphere at a temperature of from about 0° C. to about 50° C. and preferably 20° C. to 30° C. for from about 1 to 24 hours or until the reaction is essentially complete. The above reaction can be graphically illustrated as follows:

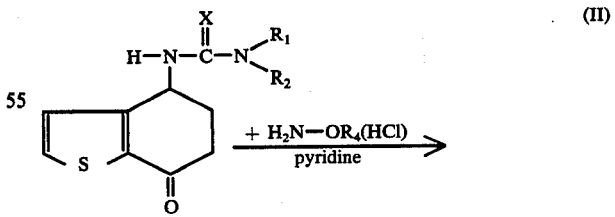

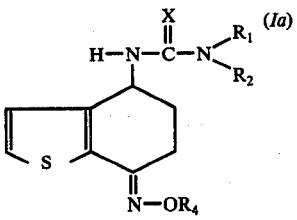

Similarly, a formula (II) tetrahydro-7-oxobenzo[b]-thien-4-ylurea can be reacted with a compound of formula $H_2N-R_3$ or an acid addition salt (preferably the hydrochloride) thereof (wherein $R_3$ is

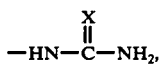

X is oxygen or sulfur and $R_1$ and $R_2$ are as defined above) under the reaction conditions hereinabove described to yield a formula (Ib) compound, by the following reaction scheme:

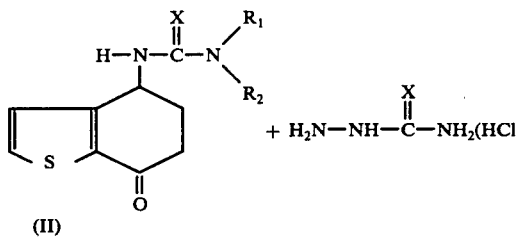

wherein X, $R_1$ and $R_2$ are as defined above.

Utilizing analogous procedures, formula (IA) 4,5,6,7-tetrahydro-7-iminobenzo[b]thien-4-ylurea compounds can be obtained wherein $R_3$ is

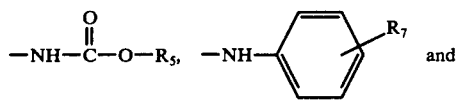

and $-N(R_5)_2$ by the following generalized reaction scheme:

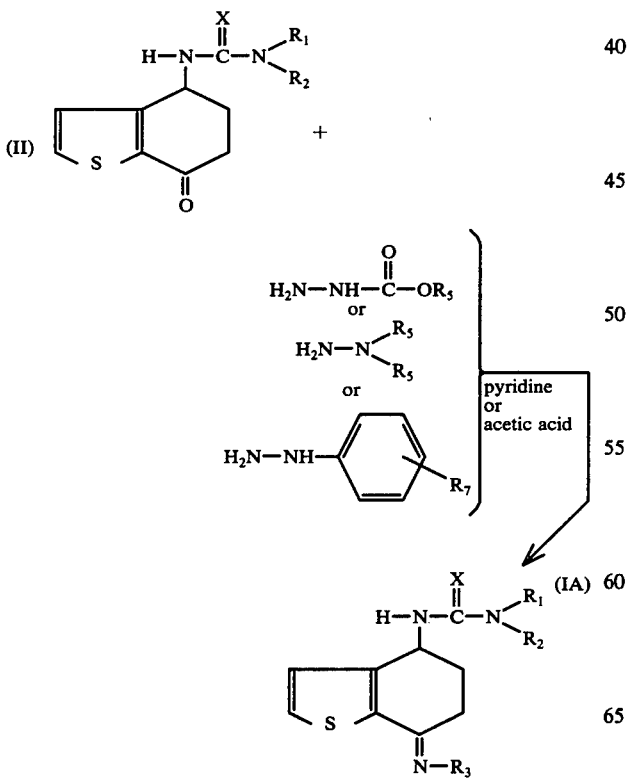

wherein X, $R_1$, $R_2$, $R_3$, $R_5$ and $R_7$ are as hereinabove defined.

Formula (IA) compounds wherein $R_3$ is

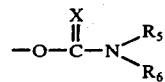

can be conveniently prepared by reacting 1 mole equivalent of the corresponding 4,5,6,7-tetrahydro-7-(hydroxyimino)benzo[b]thien-4-ylurea of formula (Ia) with a 1 to 1.2 mole equivalent of a carbamoyl halide (preferably the chloride) of the formula:

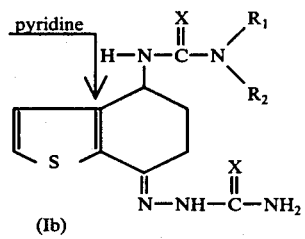

wherein X is oxygen or sulfur and $R_5$ and $R_6$ are alkyl $C_1$-$C_4$, or with an isocyanate or isothiocyanate of the formula:

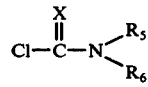

wherein X and $R_6$ are as defined above, in an anhydrous inert solvent such as tetrahydrofuran or dioxane in the presence of a base or in anhydrous pyridine under a nitrogen atmosphere at from about 0° C. to about 50° C. and preferably 20° C. to 30° C. for from 1 hour to several days until the reaction is essentially complete, by the following generalized reaction scheme:

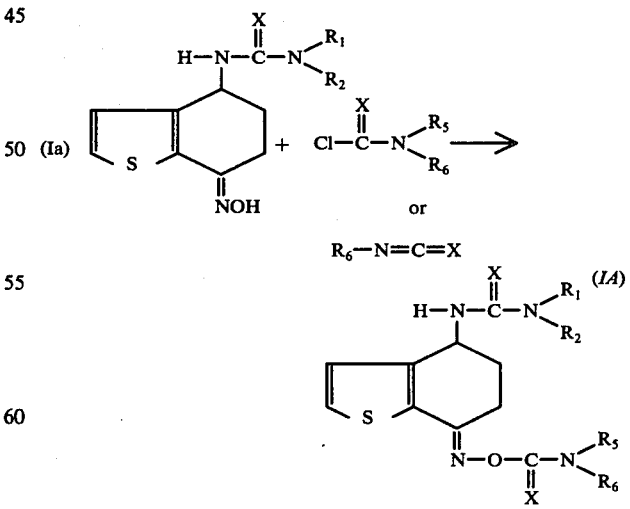

wherein $R_1$, $R_2$, $R_5$, $R_6$ and X are as defined above.

The hereinabove described and illustrated routes yield the racemic formula (IA) compounds. Should the optical isomers be desired then by substituting the levoor dextrorotatory formula (II) tetrahydro-7-oxobenzo[b]thien-4-ureas or formula (Ia) tetrahydro-7-(hydroxyimino)benzo[b]thien-4-ylureas in the above-described routes, the corresponding levo- or dextrorotatory formula (IA) tetrahydro-7-iminobenzo[b]thien-4-ylurea compounds are obtained.

An alternate route to many of the formula (IA) compounds comprises reacting 4,5,6,7-tetrahydro-7-oxobenzo[b]thiophen-4-amine of formula (III) with a compound of the formula $H_2N-R_3$ under conditions hereinabove described, wherein $R_3$ is as defined above, to obtain 4,5,6,7-tetrahydro-7-iminobenzo[b]thiophen-4-amines of formula (IV). The thus obtained formula (IV) tetrahydro-7-iminobenzo[b]thiophen-4-amines are then converted to the corresponding formula (IA) ureas by reacting said amines with (thio)cyanic acid or an alkyl iso(thio)cyanate under standard laboratory conditions well-known in the art. It will be appreciated that such a method of preparation can not be employed in those cases wherein the $R_3$ group itself contains a group reactive towards the reagents named above.

This route can be graphically illustrated as follows:

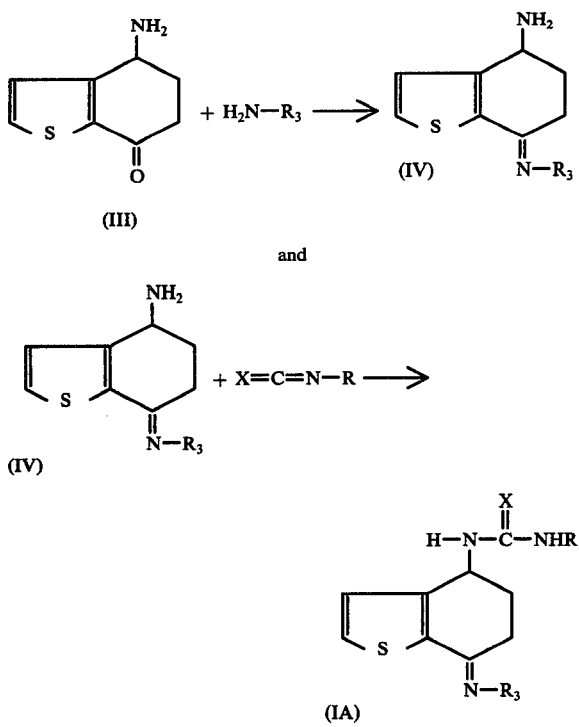

wherein X and $R_3$ are as defined above and R represents a member slected from the groups defined under $R_1$ and $R_2$ above.

The compounds of this invention are useful as growth-promoting agents for animals such as poultry, fur-bearing animals, and farm animals, and the use of said compounds for this purpose provides the added advantage of improving feed conversion for said animals. As used herein, the term "feed conversion" means the ratio of unit weight of feed per unit weight of gain and improvement in feed conversion means increased weight gain from a given unit of feed consumed.

In practice, a growth-promoting amount of a formula (IA) 4,5,6,7-tetrahydro-7-iminobenzo[b]thien-4-ylurea or an optically active isomer is administered to a host animal usually in, or with, the animal's feed. However, said compound may also be administered as a subcutaneous implant under the skin of said animal or as a parenteral injection. When administered in the feed of chickens, turkeys, sheep, cattle, goats, and the like, usually about 0.0001% to 0.08% by weight, and preferably 0.001% to 0.04% by weight of the formula (IA) urea is effective for increasing growth rate and improving feed conversion. When administered to said animals as a parenteral injection or subcutaneous implant, usually in amounts that will supply about 0.0005 mg. to 0.2 mg. and preferably 0.001 mg. to 0.10 mg per kg. of body weight per day of the active compound, will produce the desired improvement in weight gain and enhance food conversion.

If a formula (IA) active compound is to be administered to said animals in, or with, their feed, it will generally be formulated as a premix and/or feed supplement.

Premixes may be prepared by blending about 1% to 30% by weight of a formula (IA) 4,5,6,7-tetrahydro-7-iminobenzo[b]thien-4-ylurea or an optically active isomer thereof with about 70% to 99% by weight of a carrier such as ground rice hulls, rice flour, ground corn and the like.

Implants are generally in the form of a paste or pellet which releases the active compound into the bloodstream of the animal over an extended period of time; as for example, from several weeks to several months.

Pellet-type implants may be prepared by mixing from about 50% to 95% by weight of a compound of formula (IA), from about 50% to 5% by weight of a pharmaceutically acceptable carrier such as Castor wax (i.e. glyceryl 12-hydroxystearate), bees wax, white wax, starch or a high molecular weight (i.e. 4000) polyethylene glycol, or mixtures thereof, alone or in combination with other pharmacentically acceptable formulation aids such as zinc or magnesium stearate, polyvinylpyrrolidone, dibutylphthalate, and the like.

Paste implants can be prepared by using the same percentages of drug as stated above in conjunction with a mixture of high (i.e. 4000) and low (i.e. 400) molecular weight polyethylene glycols alone or in combination with the above named ingredients.

The present invention is further illustrated by the non-limiting examples set forth below, as well as testing data on typical compounds of the invention.

EXAMPLE 1

Preparation of 4,5,6,7-tetrahydro-7-(hydroxyimino)benzo[b]-thien-4-ylurea 4,5,6,7-Tetrahydro-7-oxobenzo[b]thien-4-ylurea (5 g., 0.0238 mole) and hydroxylamine hydrochloride (2 g., 0.028 mole) in dry pyridine (50 ml.) are stirred together at room temperature under nitrogen overnight. The resulting clear solution is evaporated and the residual gum triturated with water (50 ml.) and the brown solid obtained is collected, washed with water and air dried (5.15 g.). The solid is recrystallized from hot methanol to afford 2.95 g. of the title compound m.p. 232°–233° C. dec.

Similarly, levorotatory 4,5,6,7-tetrahydro-7-oxobenzo[b]thien-4-ylurea is reacted with $NH_2OH.HCl$ to afford optically active 4,5,6,7-tetrahydro-7-(hydroxyimino)benzo[b]thien-4-ylurea.

EXAMPLE 2

Preparation of 4,5,6,7-tetrahydro-7-oxobenzo[b]thien-4-ylurea, 7-semicarbazone 4,5,6,7-Tetrahydro-7-oxobenzo[b]thien-4-ylurea (3.15 g., 0.015 mole) and semicarbazide hydrochloride (2 g., 0.018 mole) are stirred in dry pyridine (35 ml.) overnight at room temperature and then heated for 1.5 hours on a steam bath. The pyridine is removed in vacuo and the residue treated with water. The precipitate is collected, washed with water and air dried to afford the title compound (3.55 g.), m.p. 245°–247° C. dec.

Similarly, thiosemicarbazide and 4,5,6,7-tetrahydro-7-oxobenzo[b]thien-4-ylurea affords 4,5,6,7-tetrahydro-7-oxobenzo[b]thien-4-ylurea, 7-thiosemicarbazone.

EXAMPLE 3

Preparation of 4,5,6,7-tetrahydro-7-oxobenzo[b]thien-4-ylurea, 0-methylcarbamoyloxime 4,5,6,7-Tetrahydro-7-(hydroxyimino)benzo[b]thien-4-ylurea (1.63 g, 0.00724 mole) and methylisocyanate (1.3 g., 0.0228 mole) are stirred in dry pyridine (26 ml.) at room temperature for 2 days. The pyridine is removed in vacuo and the residue crystallized from methanol to afford 1.35 g. of the title compound, m.p. 194°–195.5° C.

Similarly, 4,5,6,7-tetrahydro-7-(hydroxyimino)benzo[b]thien-4-ylurea is reacted with dimethylcarbamoyl chloride, ethyl isocyanate, ethyl isothiocyanate, propyl isocyanate, and butyl isocyanate to afford the following:

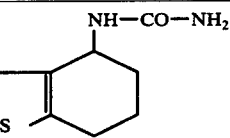

| X | $R_5$ | $R_6$ |
|---|---|---|
| O | $CH_3$ | $CH_3$ |
| O | $C_2H_5$ | H |
| S | $C_2H_5$ | H |
| O | $C_3H_7$ | H |
| O | $C_4H_9$ | H |

EXAMPLE 4

The following compounds are prepared by the method of Example 1.

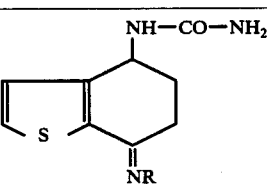

| R | Melting Point ° C. |
|---|---|
| $OCH_3$ | 262–267 dec. |
| $OC_6H_5$ | 228–229.5 dec. |
| $OCH_2C_5H_5$ | 195–198 dec. |
| $OC_4H_9$-n | |
| $OC_3H_7$-n | |
| $OC_3H_7$-i | |

EXAMPLE 5

Following the method of Example 1, 1,1-dimethyl-, 1-methyl-, 1-(n-butyl)-, 1-benzyl-, 1-allyl-, and 1-(2-propynyl)-3-(4,5,6,7-tetrahydro-7-oxobenzo [b]thien-4-yl) urea are reacted with $NH_2OH.HCl$ to afford the corresponding oxime derivatives, 1,1-dimethyl-, 1-methyl-, 1-(n-butyl)-, 1-benzyl-, 1-allyl-, and 1-(2-propynyl)-3-[4,5,6,7-tetrahydro-7-(hydroxyimino)benzo-[b]thien-4-yl]urea, respectively.

EXAMPLE 6

Preparation of 4,5,6,7-tetrahydro-7-oxobenzo [b]thien-4-ylurea, methylcarbazate 4,5,6,7-Tetrahydro-7-oxobenzo[b]thien-4-ylurea (420 mg., 0.002 mole) is stirred at room temperature overnight with methylhydrazinocarboxylate (200 mg., 0.0022 mole) in glacial acetic acid. The resulting solid is filtered and washed with ether to afford the title compound (0.5 g.) m.p. 241°–244° C. dec.

Similarly, levorotatory 4,5,6,7-tetrahydro-7-oxobenzo [b]thien-4-ylurea and methylhydrazinocarboxylate affords optically active 4,5,6,7-tetrahydro-7-oxobenzo [b]thien-4-ylurea, methylcarbazate.

Substitution of methylhydrazinocarboxylate with ethyl-, propyl-, and butylhydrazinocarboxylate affords the ethyl-, propyl-, and butylcarbazates of 4,5,6,7-tetrahydro-7-oxobenzo[b]thien-4-ylurea.

EXAMPLE 7

Preparation of 4,5,6,7-tetrahydro-7-oxobenzo[b]thien-4-ylurea, phenylhydrazone 4,5,6,7-Tetrahydro-7-oxobenzo[b]thien-4-ylurea is stirred with 20% mole excess of phenylhydrazine in methanol containing a drop of concentrated HCl to afford the phenylhydrazone of 4,5,6,7-tetrahydro-7-oxobenzo[b]thien-4-ylurea, which is collected after concentrating the reaction mixture.

In the same manner, 1-methyl-, 1,1-dimethyl-, 1-(n-butyl)-, 1-benzyl-, 1-allyl-, and 1-(2-propynyl)-3-(4,5,6,7-tetrahydro-7-oxobenzo[b]thien-4-yl)urea, phenylhydrazones are prepared by reacting the corresponding ketones with phenylhydrazine.

Substitution of other substituted phenylhydrazines in the above reaction affords the following hydrazones of 4,5,6,7-tetrahydro-7-oxobenzo[b]thien-4-ylurea: o-chlorophenylhydrazone, m-chlorophenylhydrazone, p-chlorophenylhydrazone, o-tolylhydrazone, m-tolylhydrazone, p-tolylhydrazone, o-methoxyphenylhydrazone, m-methoxyphenylhydrazone and p-methoxyphenylhydrazone, respectively.

EXAMPLE 8

Preparation 4,5,6,7-tetrahydro-7-oxobenzo[b]thien-4-ylurea, 1,1-dimethylhydrazone Following the method Example 7, 4,5,6,7-tetrahydro-7-oxobenzo[b]thien-4-ylurea is reacted with 1,1-dimethylhydrazine to afford 4,5,6,7-tetrahydro-7-oxobenzo[b]thien-4-ylurea, 1,1-dimethylhydrazone.

Similarly, levorotatory 4,5,6,7-tetrahydro-7-oxobenzo[b]thien-4-ylurea is reacted with 1,1-dimethylhydrazine to afford optically active 4,5,6,7-tetrahydro-7-oxobenzo[b]thien-4-ylurea, 1,1-dimethylhydrazone.

EXAMPLE 9

In the manner described in Example 1, 1-hydroxy-, 1-methoxy-, and 1-methyl-1-methoxy-3-(4,5,6,7-tetrahydro-7-oxobenzo[b]thien-4-yl)urea are allowed to react with $NH_2OH \cdot HCl$ to afford 1-hydroxy-, 1-methoxy-, and 1-methyl-1-methoxy-3-(4,5,6,7-tetrahydro-7-oxobenzo[b]thien-4-yl)urea, respectively.

EXAMPLE 10

Mouse Growth Regulant Tests

CFI female mice from Carworth Farm are received when they are 6 weeks old. They are housed 10 to a cage in air-conditioned rooms (72° F. to 76° F.) with automatically controlled lights, 14 hours on and 10 hours off. The basal diet used in these studies in Purina ®Laboratory Chow (see description below), which is supplied ad libitum. Water is also allowed ad libitum.

13 days after arrival, the mice are weighed in groups of 10 and assigned at random to the different treatments. The concentration of the different compounds in the diet is indicated in the following Tables. 12 Days later the mice are weighed again and the experiment terminated. At least 3 cages (30 mice) of untreated controls are included in each test. Test data are provided in Table I below wherein data are reported as percent weight gain over controls. The following is a description of the diet to which the growth promoting compounds are added.

| Diet | |
|---|---|
| Guaranteed Analysis | |
| Crude protein not less than | 23.0% |
| Crude fat not less than | 4.5% |
| Crude fiber not more than | 6.0% |
| Ash not more than | 9.0% |
| Ingredients | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. | |

TABLE I

Effectiveness of 4,5,6,7-Tetrahydro-7-iminobenzo[b]thien-4-ylureas as Animal Growth Promoting Agents Reported as Percent Weight Gain Over Controls Using Mice as the Test Animal

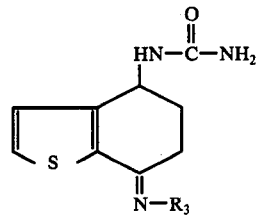

| Rate ppm. in Diet | $R_3$ | % Weight Gain Over Controls |
|---|---|---|
| 400 | $-OCH_3$ | 113 |
| 400 | $-OCH_2-\bigcirc$ | 91 |
| 400 | $-OC_2H_5$ | 84 |
| 400 | $-OH$ | 93 |
| 400 | $-HN-\overset{O}{\underset{\|}{C}}-NH_2$ | 47 |
| 400 | $-O-\overset{O}{\underset{\|}{C}}-NH-CH_3$ | 65.5 |

We claim:

1. A racemate consisting of enantiomeric 4,5,6,7-tetrahydro-7-(substituted)benzo[b]thien-4-ylureas of the formulae:

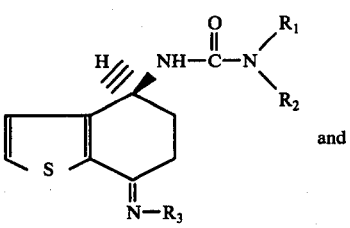

and

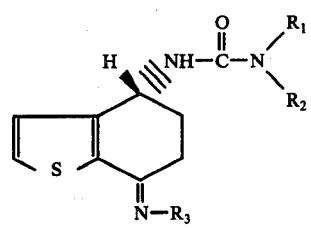

wherein $R_1$ is selected from the group consisting of hydrogen and alkyl $C_1-C_4$; $R_2$ is selected from the group consisting of hydrogen, hydroxy, alkyl $C_1-C_4$, allyl, 2-propynyl, alkoxy $C_1-C_4$ and benzyl; and $R_3$ is a moiety selected from the group consisting of those of the formulae:

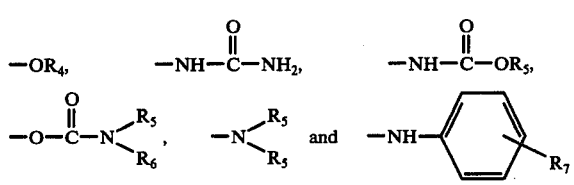

wherein $R_4$ is selected from the group consisting of hydrogen, alkyl $C_1-C_4$ and benzyl; $R_5$ is alkyl $C_1-C_4$; $R_6$ is selected from the group consisting of hydrogen and alkyl $C_1-C_4$; and $R_7$ is selected from the group consisting of hydrogen, chloro, methyl and methoxy.

2. An enantiomer selected from the group consisting of those of the formulae:

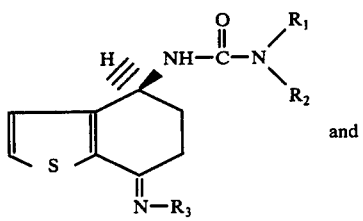

and

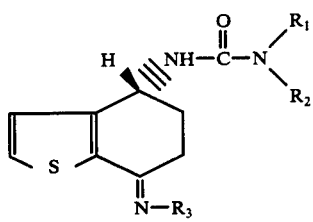

wherein $R_1$ is selected from the group consisting of hydrogen and alkyl $C_1$-$C_4$; $R_2$ is selected from the group consisting of hydrogen, hydroxy, alkyl $C_1$-$C_4$, allyl, 2-propynyl, alkoxy $C_1$-$C_4$ and benzyl; and $R_3$ is a moiety selected from the group consisting of those of the formulae:

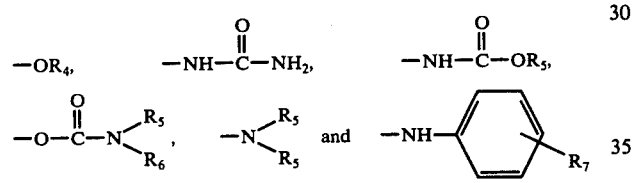

wherein $R_4$ is selected from the group consisting of hydrogen, alkyl $C_1$-$C_4$ and benzyl; $R_5$ is alkyl $C_1$-$C_4$; $R_6$ is selected from the group consisting of hydrogen and alkyl $C_1$-$C_4$; and $R_7$ is selected from the group consisting of hydrogen, chloro, methyl and methoxy.

3. A racemate consisting of enantiomeric 4,5,6,7-tetrahydro-7-(substituted)benzo[b]thien-4-ylureas of the formulae:

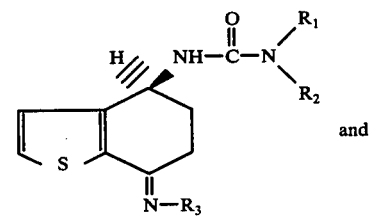

and

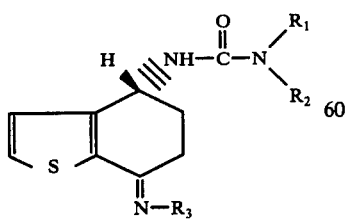

wherein $R_1$ is hydrogen or methyl; $R_2$ is hydrogen or alkyl $C_1$-$C_4$; and $R_3$ is a moiety selected from the group consisting of those of the formulae:

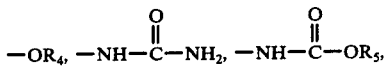

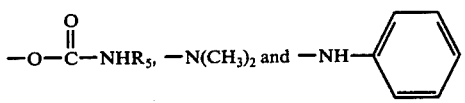

wherein $R_4$ is selected from the group consisting of hydrogen, alkyl $C_1$-$C_4$ and benzyl; and $R_5$ is alkyl $C_1$-$C_4$.

4. The racemate according to claim 3 wherein $R_1$ and $R_2$ are hydrogen and $R_3$ is hydroxy; dl-4,5,6,7-tetrahydro-7-(hydroxyimino)benzo[b]thien-4-ylurea.

5. The racemate according to claim 3 wherein $R_1$ and $R_2$ are hydrogen and $R_3$ is methoxy; dl-4,5,6,7-tetrahydro-7-(methoxyimino)benzo[b]thien-4-ylurea.

6. The racemate according to claim 3 wherein $R_1$ and $R_2$ are hydrogen and $R_3$ is ethoxy; dl-4,5,6,7-tetrahydro-7-(ethoxyimino)benzo[b]thien-4-ylurea.

7. The racemate according to claim 3 wherein $R_1$ and $R_2$ are hydrogen and $R_3$ is benzyloxy; dl-4,5,6,7-tetrahydro-7-(benzyloxyimino)benzo[b]thien-4-ylurea.

8. The racemate according to claim 3 wherein $R_1$ and $R_2$ are hydrogen and $R_3$ is ureido; dl-4,5,6,7-tetrahydro-7-oxobenzo[b]thien-4-ylurea, semicarbazone.

9. The racemate according to claim 3 wherein $R_1$ and $R_2$ are hydrogen and $R_3$ is a moiety of the formula:

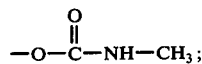

dl-4,5,6,7-tetrahydro-7-oxobenzo[b]thien-4-ylurea, O-methylcarbamoyloxime.

10. An enantiomer selected from the group consisting of those of the formulae:

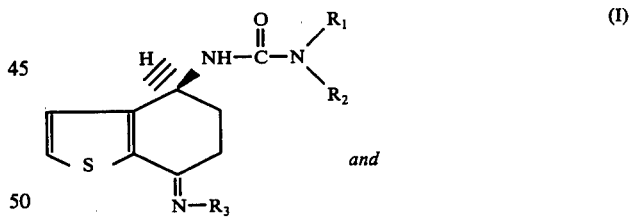

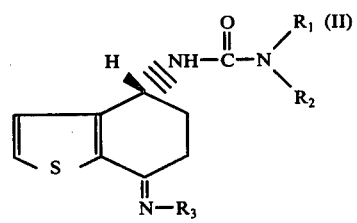

wherein $R_1$ is hydrogen or methyl; $R_2$ is hydrogen or alkyl $C_1$-$C_4$; and $R_3$ is a moiety selected from the group consisting of those of the formulae:

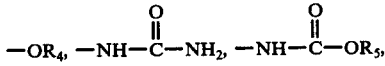

-continued

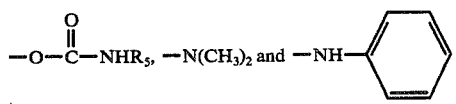

wherein R₄ is selected from the group consisting of hydrogen, alkyl $C_1$–$C_4$ and benzyl; and R₅ is alkyl $C_1$–$C_4$.

11. The enantiomer according to claim 10, formula (I) thereof, wherein R₁ and R₂ are hydrogen and R₃ is hydroxy; 4,5,6,7-tetrahydro-7-(hydroxyimino)benzo[b]-thien-4(S)-ylurea.

12. The enantiomer according to claim 10, formula (I) thereof, wherein R₁ and R₂ are hydrogen and R₃ is methoxy; 4,5,6,7-tetrahydro-7-(methoxyimino)benzo[b]-thien-4(S)-ylurea.

13. The enantiomer according to claim 10, formula (I) thereof, wherein R₁ and R₂ are hydrogen and R₃ is ethoxy; 4,5,6,7-tetrahydro-7-(ethoxyimino)benzo[b]-thien-4(S)-ylurea.

14. The enantiomer according to claim 10, formula (I) thereof, wherein R₁ and R₂ are hydrogen and R₃ is benzyloxy; 4,5,6,7-tetrahydro-7-(benzyloxyimino)benzo[b]-thien-4(S)-ylurea.

15. The enantiomer according to claim 10, formula (I) thereof, wherein R₁ and R₂ are hydrogen and R₃ is ureido; 4,5,6,7-tetrahydro-7-oxobenzo[b]thien-4(S)-ylurea, semicarbazone.

16. The enantiomer according to claim 10, formula (I) thereof, wherein R₁ and R₂ are hydrogen and R₃ is a moiety of the formula:

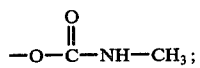

4,5,6,7-tetrahydro-7-oxobenzo[b]thien-4(S)-ylurea, O-methylcarbamoyloxime.

17. An enantiomer of the formula:

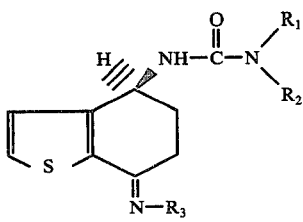

wherein R₁ is hydrogen or methyl; R₂ is hydrogen or alkyl $C_1$–$C_4$; and R₃ is a moiety selected from the group consisting of those of the formulae:

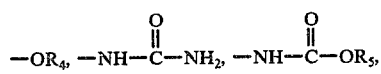

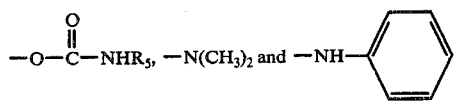

wherein R₄ is selected from the group consisting of hydrogen, alkyl $C_1$–$C_4$ and benzyl; and R₅ is alkyl $C_1$–$C_4$.

18. A method for improving feed efficiency and enhancing the growth rate of veterinary homothermic animals comprising administering to said animals an effective amount of a racemate consisting of enantiomers of the formulae:

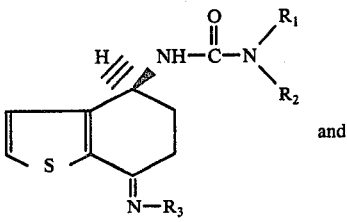

and

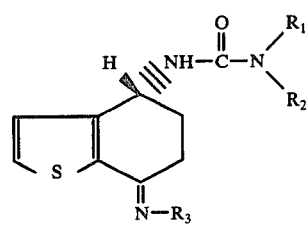

wherein R₁ is selected from the group consisting of hydrogen and alkyl $C_1$–$C_4$; R₂ is selected from the group consisting of hydrogen, hydroxy, alkyl $C_1$–$C_4$, allyl, 2-propynyl, alkoxy $C_1$–$C_4$ and benzyl; and R₃ is a moiety selected from the group consisting of those of the formulae:

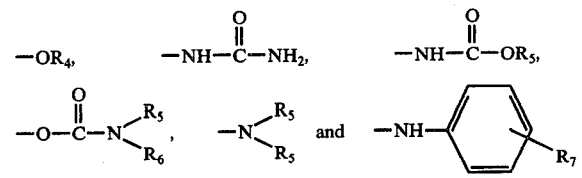

wherein R₄ is selected from the group consisting of hydrogen, alkyl $C_1$–$C_4$ and benzyl; R₅ is alkyl $C_1$–$C_4$; R₆ is selected from the group consisting of hydrogen and alkyl $C_1$–$C_4$; and R₇ is selected from the group consisting of hydrogen, chloro, methyl and methoxy.

19. A method according to claim 18 wherein said compound is parenterally administered as one or more subcutaneous implants beneath the skin of said animal, said implants being sufficient to provide a daily drug release implants being sufficient to provide a daily drug release of from 0.0005 mg. to 0.2 mg. of said compound per kg. of animal body weight.

20. A method for improving feed efficiency and enhancing the growth rate of veterinary homothermic animals comprising administering to said animals an effective amount of an enantiomer selected from the group consisting of those of the formulae:

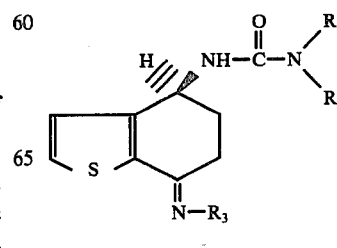

and

-continued

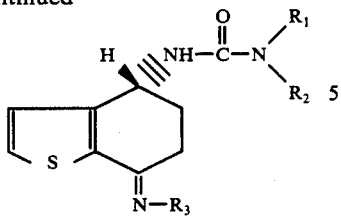

wherein $R_1$ is selected from the group consisting of hydrogen and alkyl $C_1$-$C_4$; $R_2$ is selected from the group consisting of hydrogen, hydroxy, alkyl $C_1$-$C_4$, allyl, 2-propynyl, alkoxy $C_1$-$C_4$ and benzyl; and $R_3$ is a moiety selected from the group consisting of those of the formulae:

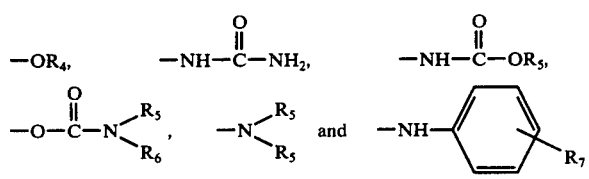

wherein $R_4$ is selected from the group consisting of hydrogen, alkyl $C_1$-$C_4$ and benzyl; $R_5$ is alkyl $C_1$-$C_4$; $R_6$ is selected from the group consisting of hydrogen and alkyl $C_1$-$C_4$; and $R_7$ is selected from the group consisting of hydrogen, chloro, methyl and methoxy.

21. A method according to claim 20 wherein said compound is parenterally administered as one or more subcutaneous implants beneath the skin of said animal, said implants being sufficient to provide a daily drug release of from 0.0005 mg. to 0.2 mg. of said compound per kg. of animal body weight.

22. An animal feed composition for improving feed efficiency and enhancing the growth rate of poultry, fur-bearing animals, and farm animals comprising a nutritionally balanced animal feed containing from 0.0001% to 0.08% by weight of a racemate consisting of enantiomers of the formulae:

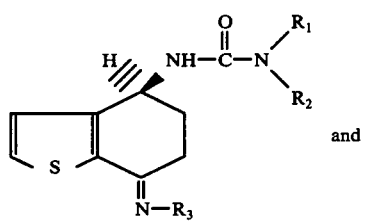

and

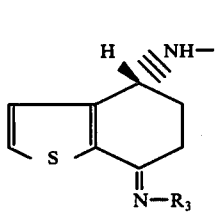

wherein $R_1$ is selected from the group consisting of hydrogen and alkyl $C_1$-$C_4$; $R_2$ is selected from the group consisting of hydrogen, hydroxy, alkyl $C_1$-$C_4$, allyl, 2-propynyl, alkoxy $C_1$-$C_4$ and benzyl; and $R_3$ is a moiety selected from the group consisting of those of the formulae:

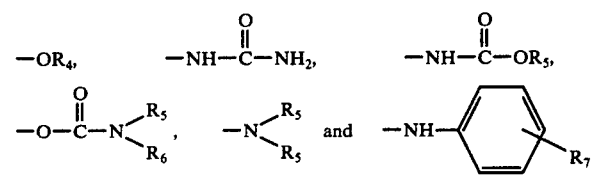

wherein $R_4$ is selected from the group consisting of hydrogen, alkyl $C_1$-$C_4$ and benzyl; $R_5$ is alkyl $C_1$-$C_4$; $R_6$ is selected from the group consisting of hydrogen and alkyl $C_1$-$C_4$; and $R_7$ is selected from the group consisting of hydrogen, chloro, methyl and methoxy.

23. An animal feed composition for improving feed efficiency and enhancing the growth rate of poultry, fur-bearing animals, and farm animals comprising a nutritionally balanced animal feed containing from 0.0001% to 0.08% by weight of an enantiomer selected from the group consisting of those of the formulae:

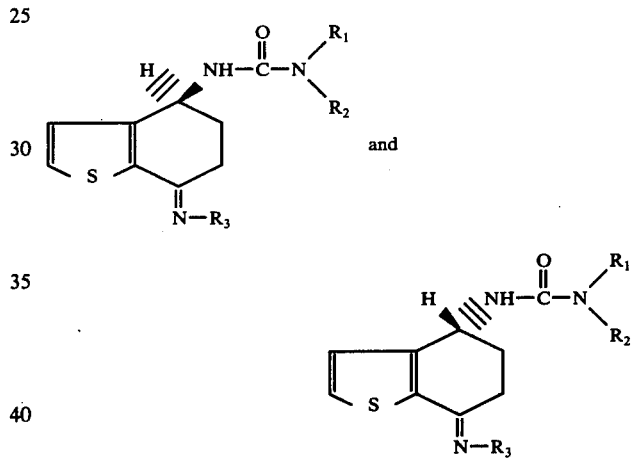

wherein $R_1$ is selected from the group consisting of hydrogen and alkyl $C_1$-$C_4$; $R_2$ is selected from the group consisting of hydrogen, hydroxy, alkyl $C_1$-$C_4$, allyl, 2-propynyl, alkoxy $C_1$-$C_4$ and benzyl; and $R_3$ is a moiety selected from the group consisting of those of the formulae:

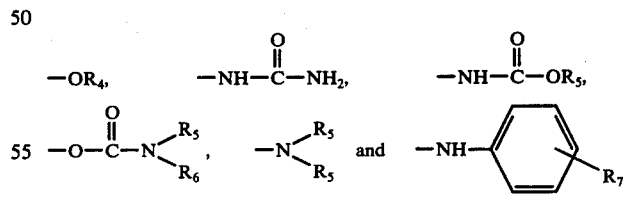

wherein $R_4$ is selected from the group consisting of hydrogen, alkyl $C_1$-$C_4$ and benzyl; $R_5$ is alkyl $C_1$-$C_4$; $R_6$ is selected from the group consisting of hydrogen and alkyl $C_1$-$C_4$; and $R_7$ is selected from the group consisting of hydrogen, chloro, methyl and methoxy.

* * * * *

UNITED STATES PATENT OFFICE
CERTIFICATE OF CORRECTION

Patent No. 4060627      Dated November 29, 1977

Inventor(s) GORO ASATO & TERENCE JAMES BENTLEY

It is certified that error appears in the above-identified patent and that said Letters Patent are hereby corrected as shown below:

Col. 11  l. 24)  "alkyl $C_1 14C_4$;" should read "alkyl $C_1-C_4$;"
Col. 11  l. 25)

Col. 12  l. 48  there should be "(I)" between the formula and the "and"

Col. 14  l. 49  the entire line reading "release implants*** daily drug" must be cancelled.

Signed and Sealed this

Seventh Day of March 1978

[SEAL]

Attest:

RUTH C. MASON
Attesting Officer

LUTRELLE F. PARKER
Acting Commissioner of Patents and Trademarks